(12) United States Patent
Cifter et al.

(10) Patent No.: US 8,906,949 B2
(45) Date of Patent: Dec. 9, 2014

(54) ORALLY DISINTEGRATING TABLETS OF ZOLMITRIPTAN AND PROCESS FOR PREPARING THE SAME

(75) Inventors: Umit Cifter, Istanbul (TR); Ali Turkyilmaz, Istanbul (TR); Gulay Yelken, Istanbul (TR)

(73) Assignee: Sanovel Ilac Sanayi Ve Ticaret Anonim Sirketi, Istanbul (TR)

( * ) Notice: Subject to any disclaimer, the term of this patent is extended or adjusted under 35 U.S.C. 154(b) by 407 days.

(21) Appl. No.: 13/111,993

(22) Filed: May 20, 2011

(65) Prior Publication Data

US 2011/0288138 A1  Nov. 24, 2011

(30) Foreign Application Priority Data

May 21, 2010 (TR) .................................. 2010004046

(51) Int. Cl.
| | | |
|---|---|---|
| *A61K 31/422* | (2006.01) | |
| *B29C 67/02* | (2006.01) | |
| *A61P 25/04* | (2006.01) | |
| *A61K 31/33* | (2006.01) | |
| *A61K 9/00* | (2006.01) | |
| *A61K 9/20* | (2006.01) | |
| *A61K 31/41* | (2006.01) | |

(52) U.S. Cl.
CPC .............. *A61K 31/33* (2013.01); *A61K 9/0056* (2013.01); *A61K 9/2009* (2013.01); *A61K 9/2013* (2013.01); *A61K 31/41* (2013.01); *A61K 31/422* (2013.01)
USPC .......................................... 514/376; 264/117

(58) Field of Classification Search
CPC .. C07D 263/20; C07D 413/10; C07D 263/24; C07D 413/12; C07D 413/14
See application file for complete search history.

(56) References Cited

U.S. PATENT DOCUMENTS

| | | | | |
|---|---|---|---|---|
| 7,387,792 | B2 * | 6/2008 | Hirsh et al. .................... | 424/472 |
| 2004/0162333 | A1 | 8/2004 | Mezaache et al. | |
| 2005/0112196 | A1 * | 5/2005 | Xie et al. ........................ | 424/464 |
| 2006/0141031 | A1 * | 6/2006 | Nelson et al. .................. | 424/464 |
| 2006/0292192 | A1 * | 12/2006 | Hasenzahl et al. ............. | 424/401 |
| 2007/0172521 | A1 * | 7/2007 | Hrakovsky ..................... | 424/451 |
| 2010/0151011 | A1 * | 6/2010 | Benke ............................ | 424/452 |
| 2011/0104288 | A1 * | 5/2011 | Thoorens et al. .............. | 424/489 |

FOREIGN PATENT DOCUMENTS

| | | |
|---|---|---|
| EP | 1246668 B1 | 11/2005 |
| WO | WO97/06162 | 2/1997 |
| WO | WO2005/075467 A2 | 8/2005 |
| WO | WO2005/115345 A1 | 12/2005 |
| WO | WO2006/092812 A2 | 9/2006 |
| WO | WO 2006092812 A2 * | 9/2006 |
| WO | WO2008/124081 A2 | 10/2008 |
| WO | WO2009/043844 A2 | 4/2009 |
| WO | WO 2009043844 A2 * | 4/2009 |
| WO | WO 2009044211 A1 * | 4/2009 |

OTHER PUBLICATIONS

Shah, Evaluation of Two New Tablet Lubricants—Sodium Stearyl Fumarate and Glyceryl Behenate, Drug Development and Industrial Pharmacy, 1986, 12(8-9), pp. 1329-1346.*
Rowe et al., Handbook of Pharmaceutical Excipients, 2006, Fifth Edition, pp. 422-425.*
English translated Search Report/Written Opinion conducted by European Patent Office (International Bureau—IB) for TR201004046 (6 pages), Nov. 25, 2010.

* cited by examiner

*Primary Examiner* — San-Ming Hui
*Assistant Examiner* — Andrew Lee
(74) *Attorney, Agent, or Firm* — Kenyon & Kenyon LLP

(57) ABSTRACT

Silicon dioxide free orally disintegrating tablet formulations of zolmitriptan or a pharmaceutically acceptable salt thereof having magnesium carbonate heavy and sodium stearyl fumarate with one or more pharmaceutically acceptable excipients and a process for preparing such a formulation and its use in the treatment of migraines.

1 Claim, No Drawings

ORALLY DISINTEGRATING TABLETS OF ZOLMITRIPTAN AND PROCESS FOR PREPARING THE SAME

CROSS REFERENCE TO RELATED APPLICATIONS

This application is based upon Turkish Patent Application No. TR201004046, filed May 21, 2010, under relevant sections of 35 USC §119, the entire contents of this application being incorporated by reference herein.

FIELD OF THE INVENTION

The present invention relates to silicon dioxide free orally disintegrating tablet formulations of zolmitriptan or a pharmaceutically acceptable salt thereof comprising magnesium carbonate heavy and sodium stearyl fumarate with one or more pharmaceutically acceptable excipients. Furthermore, the invention relates to the process for preparing such a formulation and its use in the treatment of migraines.

BACKGROUND OF THE INVENTION

Migraine is a common condition, while migraine headache is a chronic condition, prophylactic and symptomatic treatments are available. In particular, the development of selective serotonin agonists such as triptans has been a tremendous breakthrough in the treatment of migraine headaches. Zolmitriptan is one of them and is a selective 5-hydroxytryptamine 1B/1D (5-HT1B/1D) receptor agonist, which is known as (S)-4-[[3-[2-(Dimethylamino)ethyl]-1H-indol-5-yl]methyl]-2-oxazolidinone and its chemical structure is shown in the following Formula I.

Formula I

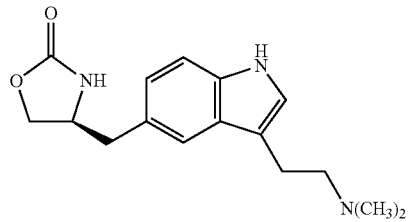

Zolmitriptan is available for oral administration in conventional and orally disintegrating tablet formulations and indicated for the acute treatment of migraine. Orally disintegrating tablets are available as Zomig-ZMT™ containing 2.5 mg or 5.0 mg zolmitriptan as active ingredient; and mannitol, microcrystalline cellulose, crospovidone, aspartame, sodium bicarbonate, citric acid anhydrous, colloidal silicon dioxide, magnesium stearate and flavor as excipients.

Various formulations and methods are already known for the preparation of orally disintegrating formulations. However, orally disintegrating formulations are becoming an increasingly important issue in the area of better patient compliance as compared to conventional solid dosage forms for oral administration, such as capsules and tablets. In particular, pediatric and geriatric patients frequently have difficulty in swallowing conventional solid dosage forms. In addition, for many medicaments, the act of swallowing the medicament often requires fluids that increase gastric volume and the likelihood of nausea and vomiting. This occurs more often in migraine patients. Perhaps the biggest advantage of orally disintegrating dosage forms is that the solid dosage form dissolves or disintegrates quickly in the oral cavity, resulting in a solution or suspension without the need for the administration of fluid. Accordingly, the patient can administer the dosage form as soon as symptoms are felt. Thus, the orally disintegrating dosage form is one of the advantageous methods to deliver the drugs such as those comprising zolmitriptan to such patients and provide a better patient compliance with recommended pharmaceutical therapies.

In addition, by administering the orally disintegrating dosage forms, faster absorption of the drug occurs through buccal mucosa and it may reduce the first pass metabolism leading to better efficacy of the drug. This dosage form enhances the clinical effects of some drugs by leading to an increase in bioavailability and a reduction in side effects because of avoidance of first-pass liver metabolism.

It is known that the development of orally disintegrating compositions are difficult for several different reasons. A satisfied orally disintegrating dosage form needs to meet number of requirements. Firstly, it has to disintegrate in the oral cavity rapidly. Moreover, a premature release in the mouth could also lead to problems due to the often unpleasant taste of the active ingredient. Besides, these compositions should be very porous and should not be very hard. These porous compositions tend to be very sensitive to humidity. As a consequence, they may have some stability problems. Finally, any orally disintegrating composition with suitable organoleptic and pharmacokinetic properties must also be manufactured at commercially useful rates and yields and using more simple methods.

To fulfill all these requirements, the formulation for a specific drug needs to be adapted in particular by a careful selection of the excipients used. However, the excipients selected may lead to formulations which are not bioavailable to the corresponding conventional dosage forms. Thus, they have to be chosen very carefully. Additionally, precautions have to be taken in the preparation, packaging, handling and storing of the finished dosage forms of orally disintegrating compositions since they tend to be both hygroscopic and friable.

Thus, various technologies have been developed which enable the preparation of compositions that disintegrate quickly in the oral cavity. These technologies include spray drying, freeze drying and floss formation. However, all of these technologies have their own limitations.

The spray drying technique involves spraying the drug and excipients into a chamber maintained at a high temperature. As a result, this technique is not suitable for application to thermo-labile drugs. Additionally, spray drying technology leads only to very poor output and is very expensive.

Freeze drying on a large scale has not been found to be very effective. Moreover, it has limitations due to factors such as time, costly equipment and processing conditions. In addition, the Zydis® tablets prepared by this technique are so fragile that the formation of the matrix material has to take place in a specific container. Tablets manufactured by this technology require a special type of packaging and careful handling during dispensing and administration to the patients, since they are prone to breakage. For example, EP 1 246 668 B1, relates to a fast acting oral pharmaceutical composition and particularly relates to fast-acting, freeze-dried pharmaceutical composition of zolmitriptan.

The floss formation technique includes compressing micro-particles of a drug and a cotton candy-like fibrous saccharide matrix, such as sucrose, dextrose, lactose and fructose. This technique is also known as Flash Dose technology (Fuisz) and requires specific equipment for making the specific matrix, which is sensitive to moisture, and generally results in tablets of high friability.

Finally, many of these techniques have proved to be only successful for specific drugs. These techniques are often not transferable to other active ingredients or may cause additional problems.

Thus, a need rises for orally disintegrating tablet formulations of zolmitriptan or a pharmaceutically acceptable salt thereof and a process for preparing such formulation which overcomes the above described problems in the prior art and having added advantages over them. Further advantages and embodiments of the present invention will become apparent from the following description.

SUMMARY AND DETAILED DESCRIPTION OF THE INVENTION

The main objective of the present invention is to provide an improved orally disintegrating tablet formulation of zolmitriptan or a pharmaceutically acceptable salt thereof useful for the treatment of migraine and associated symptoms which overcomes above described problems with using adequate excipients and which further provide the advantageous property of allowing the active medicament to disintegrate rapidly in the oral cavity without remaining substantial amounts of the active ingredient and which have a pleasant mouth feel.

Another objective of the present invention is to provide a simple, cost-effective and time saving process for the preparation of such an improved orally disintegrating tablet formulation of zolmitriptan.

Yet another objective of the present invention is to provide an orally disintegrating tablet formulation of zolmitriptan or a pharmaceutically acceptable salt thereof which has good mechanical strength (such as adequate hardness and low friability) enough to be processed in high speed tableting machines and shipped in low cost packages.

A further objective of the present invention is to provide a bioavailable and stable orally disintegrating tablet formulation of zolmitriptan or a pharmaceutically acceptable salt thereof which is stable throughout its shelf-life. According to this objective and according to this invention an orally disintegrating tablet formulation of zolmitriptan or a pharmaceutically acceptable salt thereof which is comparable with the existing conventional solid dosage forms is provided. However, unexpected benefits are found with this orally disintegrating formulation, because presentation of zolmitriptan in conventional solid or liquid oral dosage forms, having their own limitations, are not ideal for use in pediatric or geriatric patients or in patients suffering from migraine.

According to this objective, the present invention is directed to a silicon dioxide free orally disintegrating tablet formulation of zolmitriptan or a pharmaceutically acceptable salt thereof comprising magnesium carbonate heavy and sodium stearyl fumarate with one or more pharmaceutically acceptable excipient.

More specifically, the orally disintegrating tablet formulation of this invention is directed to a colloidal silicon dioxide free orally disintegrating tablet formulation of zolmitriptan or a pharmaceutically acceptable salt thereof. It is known that an improved orally disintegrating tablet formulation should have minimum grit or sandy effect, and to provide this effect silicon dioxide is used widely. However, silicon dioxides, especially colloidal silicon dioxide is very hygroscopic, causing problems when preparing the orally disintegrating tablet formulations. Thus, precautions have to be taken in the preparation, packaging, handling and storing of the finished dosage forms of orally disintegrating formulations since they tend to be both hygroscopic and friable. We have surprisingly obtained good and improved results despite of not using silicon dioxide, especially colloidal silicon dioxide. Thus, this is achieved by the adequate selection of excipients which will be further detailed below.

According to this objective, orally disintegrating tablet compositions having optimal mechanical strength are developed. The present invention addresses this need and discloses formulations that rapidly disintegrate in the oral cavity. These tablet compositions have a pleasant mouth feel and good mechanical strength. These tablets are robust (e.g., low friability, adequate hardness) enough to be processed in high speed tablet pressing machines and shipped in low cost packages, and at the same time retain rapid disintegration or dissolution properties. These orally disintegrating compositions are bioavailable in correspondence with the conventional solid dosage formulations and are stable throughout the shelf-life.

It is also known that magnesium carbonate is insoluble in carbon dioxide free water. However, in the present invention it has surprisingly been found that the specific combination of magnesium carbonate heavy and sodium stearyl fumarate with the active ingredient zolmitriptan results in a synergistic effect over the disintegration time and mechanical strength (such as: hardness and friability) of the orally disintegrating tablet formulation. According to this selection, the orally disintegrating tablet formulation of the present invention comprise magnesium carbonate heavy and sodium stearyl fumarate in a weight ratio of between 1:10 to 25:1 by weight. Preferably this ratio is 1:1 to 15:1 by weight of the total tablet weight said amount, making it possible to significantly improve compressibility, reduce friability and achieve a substantial reduction in disintegration time. Higher quantities may have negative effects on mechanical strength of the formulation and lower quantities may worsen the disintegration time.

According to this objective, the orally disintegrating tablet formulation of zolmitriptan or a pharmaceutically acceptable salt thereof comprise magnesium carbonate heavy in an amount of between 2.0 and 90.0% by weight; preferably it is 5.0 and 75.0% by weight of the total tablet weight. Thus, the hardness of the orally disintegrating tablets of the present invention is between 5 N to 100 N, preferably it is between 20 N to 50 N; and the friability of the orally disintegrating tablet is less than 1.0%, preferably it is less than 0.5%.

In another embodiment, the orally disintegrating tablet formulation comprises zolmitriptan in an amount of between 1.0 and 10.0% by weight of the total tablet weight.

It is known that magnesium stearate is also used commonly in orally disintegrating compositions but it has some disadvantages despite being a good lubricant. Magnesium stearate is practically insoluble in water and because of this hydrophobic characteristic it may retard the dissolution of a drug from a solid dosage form such as a tablet. Tablet dissolution or disintegration, especially in orally disintegrating dosage forms, is sensitive to both the amount of magnesium stearate in the formulation and the blending time. Blending time should be limited. Long blending times can result in the formulation of hydrophobic powder beds that do not disperse easily and overblending can cause compaction problems. Tablet dissolution rate and crushing strength are decreased as the time of blending is increased; and magnesium stearate may also increase tablet friability. Blending time with magnesium stearate should therefore be carefully controlled. Therefore, we achieved good results by using sodium stearyl fumarate instead of magnesium stearate. It is an extremely effective lubricant and less hydrophobic than magnesium stearate and has a less retardant effect on tablet dissolution than magnesium stearate. Sodium stearyl fumarate also doesn't have the over blending problems seen with magnesium stearate. According to this object of the invention, the present orally disintegrating tablet formulation of zolmitriptan comprises sodium stearyl fumarate in an amount of between 0.1 and 10.0% by weight, preferably it is 0.2 and 5.0% by weight of the total tablet weight.

Yet another objective of the present invention is an orally disintegrating tablet formulation of zolmitriptan which does not comprise a surfactant agent. According to this objective, said "surfactant agent" which is not used in this orally disintegrating tablet formulation may comprise but is not limited to sodium lauryl sulfate, magnesium lauryl sulfate, dioctyl sulfosuccinate, polysorbates, especially polysorbate 80, polyoxyethylene alkyl esters and ethers, glyceryl monolaurate saponins (e.g. quilllaja saponins), sorbitan laurate and the like and their mixtures thereof; preferably sodium lauryl sulfate.

Without using a surfactant agent in an orally disintegrating tablet formulation, the selection of excipients has more importance to obtain the ideal disintegrating time. Thus, crospovidone has physical and chemical properties that make it ideal for constituting the appropriate disintegrant for this invention in that crospovidone particles have a very different appearance from those of the other disintegrants. Crospovidone particles seem to consist of aggregates of smaller particles that are fused together. This aggregation gives crospovidone a spongy, highly porous appearance and it swells very little, yet takes water into its network quite rapidly. This helps crospovidone to dissolve easily and quickly in a little amount of water or saliva and makes its disintegrating rate much faster than other related excipients.

According to this embodiment of the invention, the orally disintegrating tablet formulation further comprises crospovidone in an amount of between 0.5 to 30.0% by weight, preferably in an amount of 5.0 to 20.0% by weight of the total formulation and the formulation disintegrates in oral cavity in less than 60 seconds, preferably in less than 30 seconds and more preferably in less than 20 seconds.

In a further embodiment, the orally disintegrating tablet formulation of zolmitriptan or a pharmaceutically acceptable salt thereof comprises one or more pharmaceutically acceptable excipients other than magnesium carbonate heavy, sodium stearyl fumarate and crospovidone wherein the one or more pharmaceutically acceptable excipients are selected from the group comprising at least one of dispersing agents, diluents, binders, sweeteners, flavoring agents and coloring agents.

Suitable dispersing agents may comprise but are not limited to calcium silicate, magnesium aluminum silicate and the like and mixtures thereof.

Suitable diluents may comprise but are not limited to mannitol, microcrystalline cellulose, lactose, starch, sodium carbonate, sodium bicarbonate, calcium carbonate and the like and mixtures thereof; preferably mannitol and/or microcrystalline cellulose are used. In contrast to prior art formulations it is not necessary to use a highly-compressible quality of mannitol, such as spray-dried mannitol which is also more expensive than mannitol. According to this embodiment of the invention, the orally disintegrating tablet formulation of zolmitriptan comprises mannitol, wherein it is present in an amount of between 2.0 to 90.0% by weight, preferably it is 10.0 to 75.0% by weight of the total tablet weight.

It has been found that when the weight ratio of mannitol to microcrystalline cellulose is in the range of between 1:10 and 10:1 (w/w), it has a synergistic effect over the stability of the orally disintegrating composition. Preferably the range of weight ratio is between 1:5 and 5:1 (w/w).

Suitable binders may include but are not limited to polyvinyl pyrrolidone, polyethylene glycol, polyvinyl alcohol, polyvinyl acetate, cellulose derivatives such as hydroxypropyl methyl cellulose, carboxy methyl cellulose, methyl cellulose, gelatin, carrageenan, guar gum, xanthan gum and the like and mixtures thereof; preferably it is polyvinylpyrrolidone. Polyvinyl pyrrolidone content is about from 1 to 10%, preferably about from 2 to 5% by weight of total composition.

The orally disintegrating compositions of this invention comprises sucralose as a sweetener to improve patient compliance. In the prior art, it is know that aspartame is used mostly as a sweetener but contradictory to the prior art we have found that the effect of sucralose as a sweetener in this formulation not only helped to improve its taste, but also increased the efficacy and the convenience of the formulation. In addition, sucralose has positive effect over the glycemic index. There are many disadvantages concerning aspartame and it has a limited usage if you have to use it every day and also there are several incompatibilities reported in literature and safety problems. Thus, sucralose has an important role in this aspect and even if used in low amounts, it has a synergistic taste improvement with mannitol which is also a very important issue in orally disintegrating tablet formulations. According to this objective of the present invention, sucralose is present in an amount of between 0.01 and 5.00% by weight, and preferably it is 0.05 and 2.00% by weight of the total tablet weight.

Suitable flavoring agents may comprise but are not limited to fruit flavors such as orange, banana, strawberry, cherry, wild cherry, lemon; and other flavors such as cardamom, anise, peppermint, menthol, vanillin and ethyl vanillin and the like and mixtures thereof. Preferably, the flavoring agent is a fruit flavor such as orange. In one aspect, the flavoring agent content is present in an amount of from 0.05 to 5.0% by weight of the total tablet weight.

Suitable coloring agents are selected from the group comprising iron oxides (such as iron oxide yellow, red or black), Food, Drug & Cosmetic (FD&C) dyes, poncau, indigo blue, indigotine blue, carmoisine indigotine, quinoline yellow, flaming red, carmine, carmoisine, sunset yellow and the like and mixtures thereof. Preferably, the coloring agent is iron oxide yellow. According to one aspect, a coloring agent is used optionally and may be present in an amount of from 0.01 to 1.00% by weight of the total tablet formulation.

As it is mentioned above, developing orally disintegrating compositions are difficult due to several different factors. A satisfied orally disintegrating dosage form needs to meet number of requirements. Firstly, it has to disintegrate in the oral cavity rapidly. Moreover, a premature release in the mouth could also lead to problems due to the often unpleasant taste of the active ingredient. Besides, these compositions should be very porous and should not be very hard. These porous compositions tend to be very sensitive to humidity. As a consequence, they may have some stability problems.

However, in order to be pharmacologically acceptable, orally disintegrating compositions must be palatable, e.g., have acceptable organoleptic properties such as good taste and mouthfeel, because orally disintegrating compositions are designed to disintegrate in the oral cavity of the patient rapidly without remaining substantial amounts of the active ingredient. In addition, the orally disintegrating formulations must also provide acceptable pharmacokinetics and bioavailability to provide the desired therapeutic effect. Conversely, components of the formulation that promote rapid release may result in undesirable taste or mouthfeel properties.

Finally, any orally disintegrating composition with suitable organoleptic and pharmacokinetic properties must also be manufactured at commercially useful rates and yields.

To fulfil all these requirements the formulation for a specific drug needs to be adapted in particular by a careful selection of the excipients used. However, the excipients selected may lead to formulations which are not bioavailable to the corresponding conventional dosage forms. Thus, the excipients have to be chosen very carefully.

In this present invention, to minimize the disintegration time and maximize the mechanical resistance of the tablets, this orally disintegrating tablet formulation has been designed, comprising the following:

a) 1.0 to 10.0% by weight of zolmitriptan or a pharmaceutically acceptable salt thereof;

b) 2.0 to 90.0% by weight of mannitol;

c) 2.0 to 90.0% by weight of magnesium carbonate heavy;

d) 0.5 to 30.0% by weight of crospovidone;

e) 0.1 to 10.0% by weight of polyvinyl pyrrolidone;

f) 0.01 to 5.00% by weight of sucralose;

g) 0.05 to 5.0% by weight of flavoring agent; and h) 0.1 to 10.0% by weight of sodium stearyl fumarate.

According to further objective of the invention, the preferred process of the present invention for preparing the above orally disintegrating tablet formulation of zolmitriptan or a pharmaceutically acceptable salt thereof comprises the following steps:

a) sieving zolmitriptan and magnesium carbonate heavy and mixing them;

b) dissolving polyvinyl pyrrolidone in water and/or alcohol to form a polyvinyl pyrrolidone solution;

c) granulating the mixture with the solution;

d) sieving and drying the wet granules and milling the dried granules;

e) adding mannitol, crospovidone, sucralose and flavoring agent and mixing them;

f) adding sodium stearyl fumarate to this mixture and blending them until obtaining a homogenous powder mixture; and g) compressing the blended mixture to form tablets.

In a further aspect, the present invention shows that it is possible to have a significant influence on the disintegration rate of the tablet by modifying the dimensions and shape of the tablet. In general, as the tablet becomes thinner and has higher porosity, the orally disintegrating composition will be weakened faster when it contacts with saliva because the disintegration process is produced after wetting all the surface of the tablet via capillary action. Also, any shape which maximizes the contact surfaces with the saliva may produce a significant reduction in disintegration time.

The preferred shape of the orally disintegrating tablet composition of this invention may have a shape of a disk, circle, round, sphere, donut, bar, polygon, ellipse and the like. The preferred shape of the tablet is a flat round shape.

This invention is further defined by reference to the following examples. Although the examples are not intended to limit the scope of the present invention, it should be considered in the light of the description detailed above. It will be apparent to those skilled in the art that many modifications, both to materials and methods, may be practiced without departing from the scope of the invention.

EXAMPLES

Example 1

Orally Disintegrating Zolmitriptan Tablets

| Ingredients | Amount % |
| --- | --- |
| Zolmitriptan | 2.5 |
| Magnesium carbonate heavy | 20.0 |
| Mannitol | 58.30 |
| Polyvinyl pyrrolidone | 1.00 |
| crospovidone | 15.00 |
| sucralose | 0.20 |
| Orange flavor | 1.00 |
| Sodium stearyl fumarate | 2.00 |
| Total tablet weight | 100.0 |

Wet granulation techniques may result in cores of a high hardness which make it difficult to obtain fast dissolving and fast disintegrating tablets. Moreover, tablets prepared thereby often lead to coarse dispersions in the oral cavity resulting in a poor patient compliance. Therefore, the manufacturing process has importance by the selection of adequate excipients. This example is manufactured by a wet granulation technique which is described above in the description and good results have obtained such as disintegration time, adequate hardness and low friability. Zolmitriptan and magnesium carbonate heavy is sieved and then mixed. Polyvinyl pyrrolidone is granulated in water and/or alcohol to form a polyvinyl pyrrolidone solution. The mixture is granulated with the solution and wet granules are sieved and dried and the dried granules are milled. Mannitol, crospovidone, sucralose and orange flavor are added and then mixed. Sodium stearyl fumarate is added to this mixture and blended together until obtaining a homogenous powder mixture. This blended mixture is compressed to form tablets.

Example 2

Orally Disintegrating Zolmitriptan Tablets

| Ingredients | Amount % |
| --- | --- |
| Zolmitriptan | 2.5 |
| Mannitol | 50.0 |
| Microcrystalline cellulose | 29.30 |
| Sucralose | 0.20 |
| Orange flavor | 1.00 |
| crospovidone | 15.00 |
| Sodium stearyl fumarate | 2.00 |
| Total tablet weight | 100.0 |

This formulation is prepared by direct compression. Firstly, zolmitriptan, mannitol, microcrystalline cellulose, crospovidone, sucralose and orange flavor is sieved and then blended together until having a homogenous mixture. Sodium stearyl fumarate is then sieved and added to this mixture and blending all together until obtaining a homogenous powder mixture. This blended mixture is compressed to form tablets.

Example 3

Orally Disintegrating Zolmitriptan Tablets

| Ingredients | Amount % |
|---|---|
| Zolmitriptan | 2.5 |
| Ludiflash | 79.30 |
| Sucralose | 0.20 |
| Orange flavor | 1.00 |
| crospovidone | 15.00 |
| Sodium stearyl fumarate | 2.00 |
| Total tablet weight | 100.0 |

This formulation is prepared by direct compression. Firstly, zolmitriptan, mannitol, crospovidone, Ludiflash (mannitol 90%, crospovidone 5%, polyvinyl acetate 5%), sucralose and orange flavor is sieved and then blended together until having a homogenous mixture. Sodium stearyl fumarate is then sieved and added to this mixture and blending all together until obtaining a homogenous powder mixture. This blended mixture is compressed to form tablets.

Example 4

Orally Disintegrating Zolmitriptan Tablets

| Ingredients | Amount % |
|---|---|
| Zolmitriptan | 2.5 |
| Calcium silicate | 20.0 |
| Mannitol | 58.30 |
| Polyvinyl pyrrolidone | 1.00 |
| crospovidone | 15.00 |
| sucralose | 0.20 |
| Orange flavor | 1.00 |
| Sodium stearyl fumarate | 2.00 |
| Total tablet weight | 100.0 |

This formulation is prepared by wet granulation as described above. Zolmitriptan and calcium silicate is sieved and then mixed. Polyvinyl pyrrolidone is granulated in water and/or alcohol to form a polyvinyl pyrrolidone solution. The mixture is granulated with the solution and wet granules are sieved and dried and the dried granules are milled. Mannitol, crospovidone, sucralose and orange flavor are added and then mixed. Sodium stearyl fumarate is added to this mixture and blended together until obtaining a homogenous powder mixture. This blended mixture is compressed to form tablets.

According to standardized methods and equipment for testing friability, hardness and disintegrating time have been provided in European Pharmacopeia. These orally disintegrating tablet formulations of the invention (Ex. 1 to 4) are tested according to these methods. As it is seen in the following Table 1, the hardness of the tablets is quite sufficient to allow easy and convenient removal from the package without breaking the dose unit. These orally disintegrating tablets are hard enough to be handled and packaged like conventional tablets. They are compressed to a hardness of 20-50 Newton and possess a friability of less than 1%. The disintegrating times are acceptable and the taste and mouthfeel of the tablets are good.

Orally disintegrating tablets of these examples (Ex. 1 to 4) are also tested according to their "Carr compressibility" and "angle of response" as they are shown in Table 1. Common indices of flowability are the Carr index and the angle of response. The increase in bulk density of a powder is related to the cohesiveness of a powder. Measurement of the bulk density of a powder is essential to define the flow characteristics. The Can index provides guidance for powder flowability. A lower Can index of excipients is more desirable for acceptable powder flow. Can Index Classification and Powder Flowability is shown below;

| Carr Index (compressibility) | (%) Flow |
|---|---|
| 5-12 | Free flowing |
| 12-16 | Good |
| 18-21 | Fair |
| 23-35 | Poor |
| 33-38 | Very poor |
| >40 | Extremely poor |

"Angle of response" is a common method used to measure powder flow with small sample quantity. Angles less than 30° are usually indicative of good flow, while powders with angles greater than 40° are likely to be problematic. The ultimate goal of flow analysis is to identify the powder or powder blend that provides the least weight variation in the finished tablet. The more fluid the powder has, the more efficiently and reproducibly it should fill the die cavities of a tablet press. This more efficient and reproducible die fill should be reflected in increased tablet weights and reduced intertablet weight variation.

TABLE 1

| Examples | 1 | 2 | 3 | 4 |
|---|---|---|---|---|
| Hardness (Newton) | 30 | 35 | 40 | 32 |
| Friability (%) | 0.15 | 0.20 | 0.29 | 0.18 |
| Disintegration time (sec) | 15 | 17 | 18 | 16 |
| Carr Compressibilty (%) | 10 | 16 | 16 | 13 |
| Angle of response | ≤30° | ≤30° | ≤30° | ≤30° |

The invention claimed is:
1. An orally disintegrating tablet formulation of zolmitriptan or a pharmaceutically acceptable salt thereof consisting of:
  a) 1.0 to 10.0% by weight of zolmitriptan or a pharmaceutically acceptable salt thereof;
  b) 2.0 to 90.0% by weight of mannitol;
  c) 2.0 to 90.0% by weight of magnesium carbonate heavy;
  d) 0.5 to 30.0% by weight of crospovidone;
  e) 0.1 to 10.0% by weight of polyvinylpyrrolidone;
  f) 0.01 to 5.00% by weight of sucralose;
  g) 0.05 to 5.0% by weight of flavoring agent; and
  h) 0.1 to 10.0% by weight of sodium stearyl fumarate.

* * * * *